(12) United States Patent
Tejani

(10) Patent No.: US 10,258,453 B2
(45) Date of Patent: Apr. 16, 2019

(54) PEDAL THROMBOEMBOLIC PROTECTION DEVICE

(71) Applicant: Furqan Tejani, Yonkers, NY (US)

(72) Inventor: Furqan Tejani, Yonkers, NY (US)

( * ) Notice: Subject to any disclaimer, the term of this patent is extended or adjusted under 35 U.S.C. 154(b) by 217 days.

(21) Appl. No.: 14/716,706

(22) Filed: May 19, 2015

(65) Prior Publication Data

US 2016/0338820 A1 Nov. 24, 2016

(51) Int. Cl.
*A61F 2/01* (2006.01)

(52) U.S. Cl.
CPC .............. *A61F 2/01* (2013.01); *A61F 2/013* (2013.01); *A61F 2002/011* (2013.01); *A61F 2002/016* (2013.01); *A61F 2230/0067* (2013.01)

(58) Field of Classification Search
CPC .............. A61F 2/013; A61F 2002/016; A61F 2230/0067
See application file for complete search history.

(56) References Cited

U.S. PATENT DOCUMENTS

| | | | | |
|---|---|---|---|---|
| 2010/0114017 A1* | 5/2010 | Lenker | ............. | A61B 17/12118 604/96.01 |
| 2010/0217276 A1* | 8/2010 | Garrison | ............. | A61M 1/3613 606/128 |
| 2011/0160757 A1* | 6/2011 | Ferrera | ................ | A61B 17/221 606/159 |
| 2015/0202037 A1* | 7/2015 | Sullivan | ................. | A61F 2/013 606/200 |

* cited by examiner

*Primary Examiner* — Diane D Yabut
(74) *Attorney, Agent, or Firm* — Schwabe, Williamson & Wyatt, P.C.

(57) ABSTRACT

Disclosed herein are embolism protection devices that may be deployed in the peripheral arterial system for the collection of loosened or floating debris, such as embolic material dislodged during or thrombi formed as a result of a peripheral intervention, such as an angioplasty, stenting, or atherectomy. The disclosed embolism protection devices are designed to be inserted distal to lesion in a lower limb artery via one of the arteries of the foot, such as the dorsalis pedis, posterior tibialis, or peroneal (fibular) artery, and they include a compliant mesh portion supported by a compliant wire support member, and the compliant mesh portion extends to form or couples to a solid catheter portion that extends out of the body during use, and that may be coupled to a stopcock or syringe for removal of debris.

6 Claims, 7 Drawing Sheets

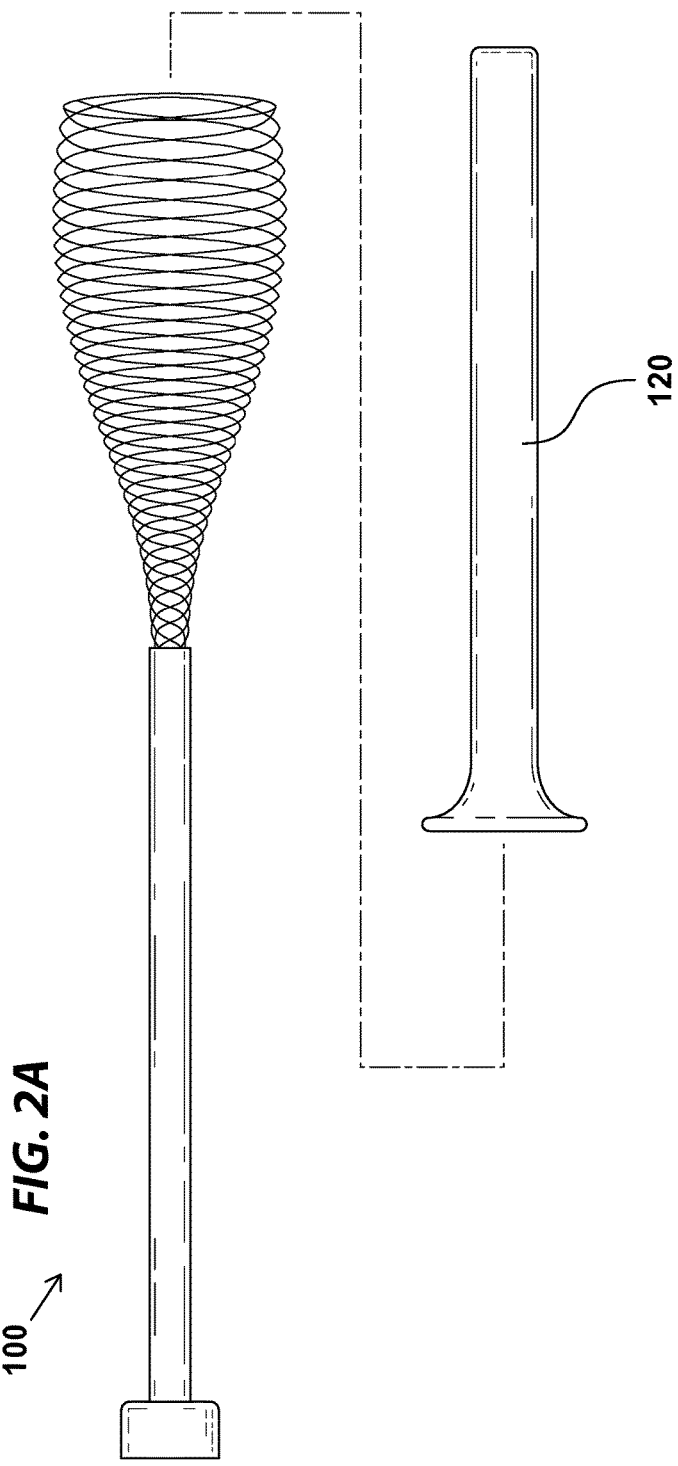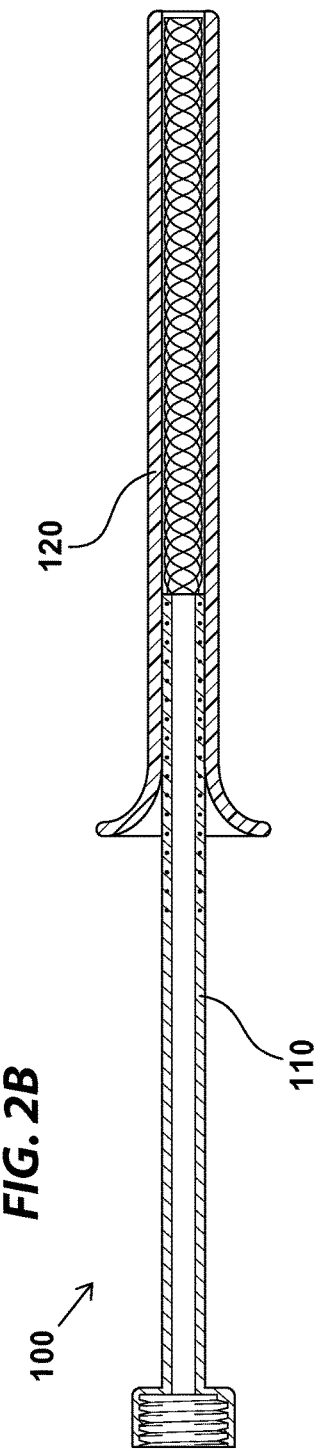

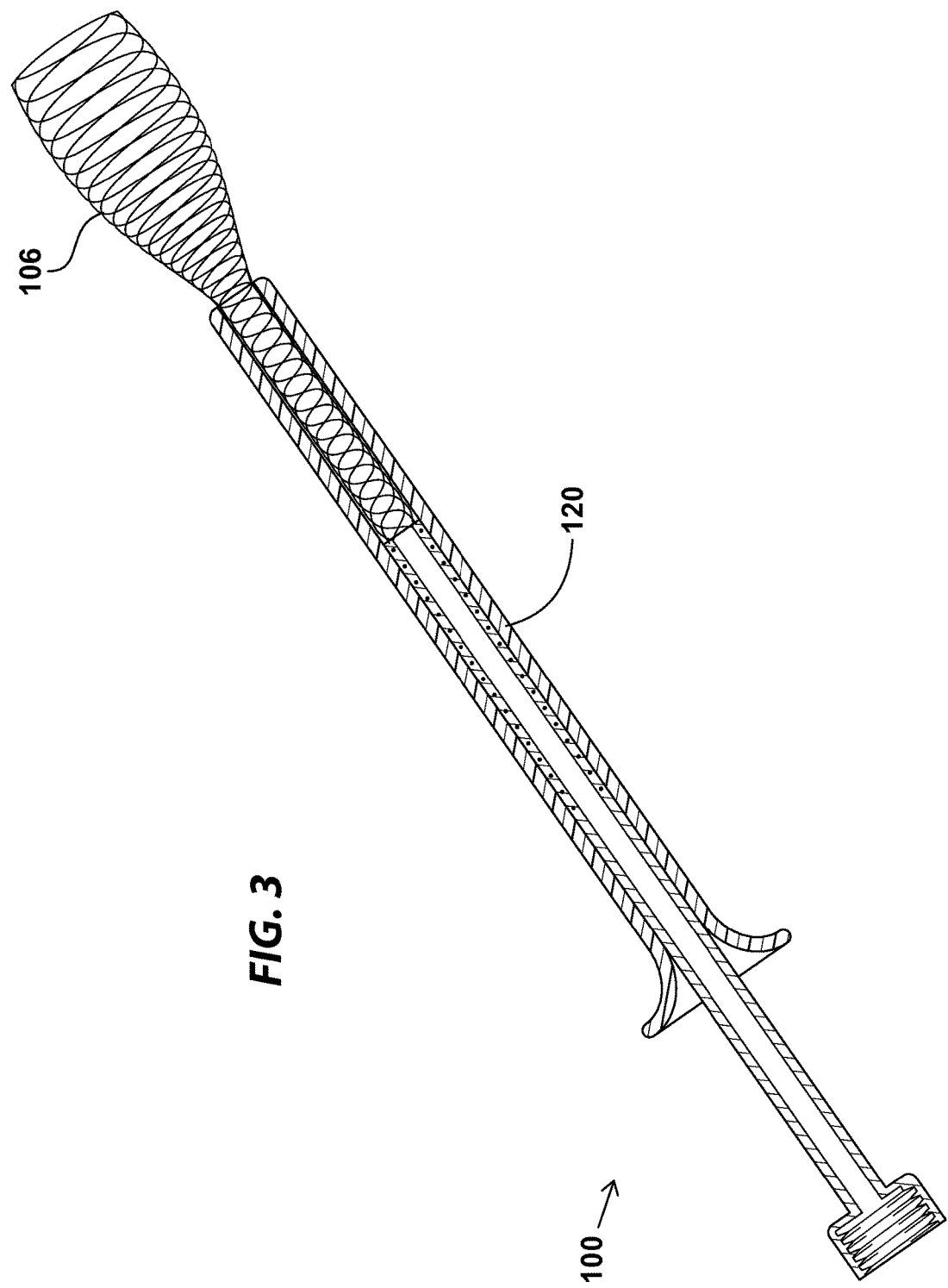

PEDAL THROMBOEMBOLIC PROTECTION DEVICE

TECHNICAL FIELD

Embodiments relate to a thromboembolic protection device that prevents the free flow of embolism-creating particles that are created during peripheral vascular interventions.

BACKGROUND

Peripheral artery disease (PAD) includes stenosis and occlusion of upper- or lower-extremity arteries due to atherosclerotic or thromboembolic disease. PAD represents a spectrum of disease severity, encompassing both asymptomatic and symptomatic disease. In PAD, as blood vessels narrow, arterial flow into the extremities worsens, and symptoms may manifest either as classic intermittent claudication (IC) or as atypical claudication or leg discomfort. As the disease progresses, patients may develop more severe claudication, with reduced walking distance and eventually with rest pain. In 5 to 10 percent of cases, claudication progresses to a worsened severity of the disease, called critical limb ischemia (CLI)—defined as ischemic rest pain for more than 14 days, ulceration, or tissue loss/gangrene. Patients with CLI have a mortality of 25 percent at one year.

Multiple types of interventions are used for revascularization in patients with PAD, including open surgery, angioplasty (e.g., cryoplasty or angioplasty with drug-coated, cutting, or standard angioplasty balloons), stenting (e.g., with self-expanding or balloon-expandable stents are available), and atherectomy (e.g., using laser, directional, orbital, or rotational atherectomy devices). With improvements in endovascular techniques and equipment, the use of balloon angioplasty, stenting, and atherectomy has led to application of endovascular revascularization to a wider range of patients, both among those with more severe symptoms and those with less severe symptoms. However, such interventions frequently involve first traversing a stenosis with a wire, catheter, or treatment device, which poses a risk of embolizing debris even prior to the intervention

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 2A and 2B include an exploded view (FIG. 2A) and a cross-sectional view (FIG. 2B) illustrating how the embolism protection device shown in FIGS. 1A and 1B may be maintained in a compressed state inside a deployment catheter;

FIG. 3 illustrates the embolism protection device shown in FIGS. 1A and 1B in the process of being deployed from the deployment catheter;

DETAILED DESCRIPTION OF DISCLOSED EMBODIMENTS

Figure 1A:
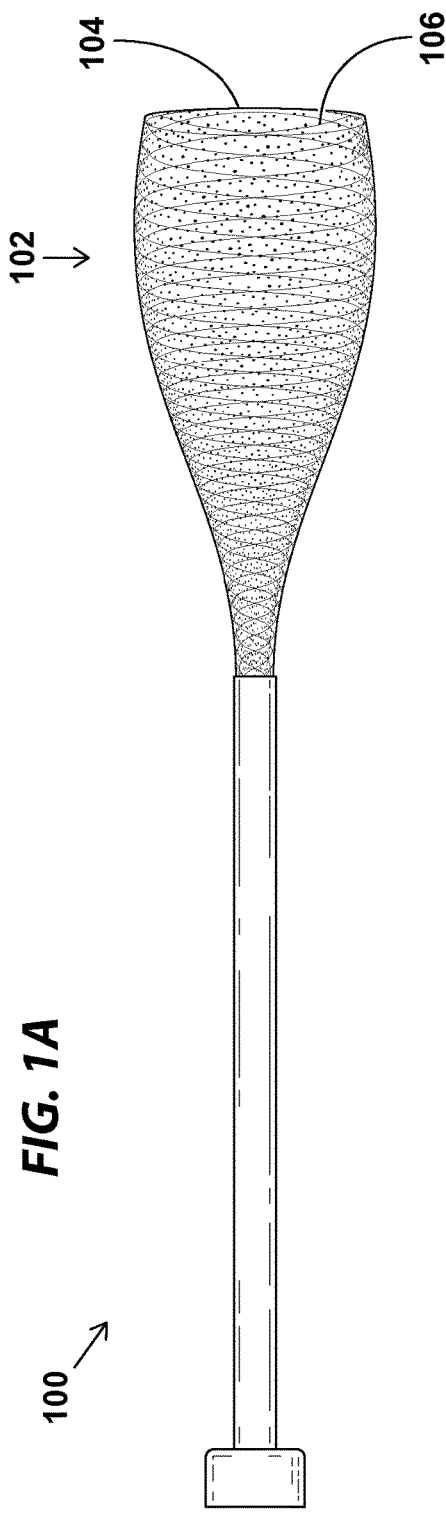
FIGS. 1A and 1B illustrate an example of an embolism protection device in an expanded state, shown in a perspective view (FIG. 1A) and a partial cutaway view (FIG. 1B)

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide embolism protection devices that may be deployed in the peripheral arterial system for the collection of loosened or floating debris, such as embolic material dislodged during or thrombi formed as a result of a peripheral intervention, such as an angioplasty, stenting, or atherectomy. Prior to the present disclosure, most of the filters used to prevent embolism during or after peripheral interventions were devices that were advanced through the vasculature from above (e.g., proximal to) the lesion, and deployed into the anatomy distal to the lesion. During this process, the filter and the wire had to traverse the lesion in order to be placed, which created a risk of embolization even prior to the intervention.

By contrast, various embodiments disclosed herein are embolism protection devices that are designed to be inserted distal to lesion in a lower limb artery via one of the arteries of the foot, such as the dorsalis pedis, posterior tibialis, or peroneal (fibular) artery. In various embodiments, this approach may obviate the problem of needing to traverse lesions to place a filter device, and it therefore may avoid the risk of dislodging the detritus that could cause an embolism.

Once positioned, the embolism protection device may be allowed to open such that it filters the blood and excludes any plaques, thrombi, or other emboli that may be dislodged, for example due to mechanical and drag forces exerted upon them as devices traverse the area of plaque or stenosis. Thus, in various embodiments, the device may prevent atherosclerotic material and other debris from entering the circulation, and may protect the subject from embolism associated with peripheral interventions.

An embolus can be any particle comprising a foreign or native material that enters the vascular system with potential to cause occlusion of blood flow. Emboli can be formed from aggregated fibrin, red blood cells, collagen, cholesterol, plaque, fat, calcified plaque, bubbles, arterial tissue, and/or other miscellaneous fragments. Each dislodged fragment, or embolus, is carried along by the blood flow until it becomes lodged or trapped in a smaller vessel and occludes blood flow, creating an embolism. Since emboli reduce or cut off blood flow, damage to the body may result, such as tissue damage.

In various embodiments, the embolism protection device may have a first (distal) portion formed from a thin, compliant mesh material having a pore size that is sufficiently large to allow blood to flow freely therethrough, but that is sufficiently small to prevent potential thrombi and emboli from passing through. In various embodiments, the thin, compliant mesh material may be made from Nitinol™, and in some embodiments, it may have a slippery surface to ease the insertion of the device into the vascular system. In various embodiments, the compliant mesh material may be supported by a compliant wire support member that may be formed from a material having a shape memory function, such as Nitinol™ wire. In various embodiments, the compliant wire support member may be coupled to or otherwise configured to stabilize and/or stretch the compliant mesh material. In some embodiments, the compliant wire support member may be biased to adopt an open configuration (e.g., having a larger diameter in the open state than in the closed state), and may be sized and shaped to secure or stretch or open the compliant mesh material to abut the full circumference of an arterial wall.

In various embodiments, the compliant mesh material and compliant wire support member also may be compressed or collapsed to adopt a very small outer circumference and/or outer diameter, for instance by being inserted into the lumen of a small diameter deployment catheter, such that the collapsed embolism protection device may be advanced to a desired part of the peripheral arterial system.

In some embodiments, the compliant mesh filter portion of the embolism protection device may be generally conical or cup-shaped, and the apex of the cone or cup may have an opening that extends to form (or couples to) a slender, solid-walled catheter portion having a lumen extending therethrough. In some embodiments, the aperture in the apex of the cone or cup shaped mesh filter portion may communicate with the lumen of the catheter portion, for example, so that debris captured in the mesh filter may be evacuated from the body via the catheter portion. In some embodiments, the proximal end of the catheter portion (e.g., nearest the physician and outside the body) may include a threaded or Luer-lock coupling mechanism, for example for coupling to a syringe or stopcock. In some embodiments, the syringe or stopcock may be used to draw debris captured by the embolism protection device through the catheter portion and out of the body.

In various embodiments, in order to place the embolism protection device, access is gained with a needle in one of the arteries of the foot, such as the dorsalis pedis, posterior tibialis, or peroneal (fibular) artery, and a small wire, such as a 0.014 inch wire, is inserted into the artery and advanced to a position distal to the lesion. In various embodiments, the needle is then withdrawn, leaving the wire in place. The embolism protection device may then be advanced (in a compressed state inside a deployment catheter) over the wire. In various embodiments, the wire may be withdrawn once the filter is in place, and before the embolism protection device is unsheathed.

In various embodiments, once the embolism protection device has been placed in an appropriate position, the deployment catheter may be slowly withdrawn, unsheathing the device progressively until the device is fully unsheathed. In various embodiments, unsheathing the embolism protection device may allow the compliant wire support member to fully open the compliant mesh portion abut against the walls of the artery, thus preventing any debris from passing beyond that point. In various embodiments, the compliant mesh portion and the compliant wire support member are positioned entirely within the artery, while the catheter portion extends out of the body.

In various embodiments, a stopcock or syringe may be coupled to the outside (proximal) portion of the device to cause hemostasis, and in various embodiments, the stopcock may can be opened periodically or the syringe used to withdraw blood and debris to keep the filter clear of debris. In various embodiments, upon completion of the procedure, the embolism protection device may be simply pulled out in its expanded state because, due to the low profile and pliable material of the device, the injury potential is very low. Alternatively, in various embodiments, the embolism protection device may be resheathed and the device withdrawn in its compressed state.

In various embodiments, the mesh material of the compliant mesh portion may have a pore size that is sized to allow vessel perfusion (e.g., that allows the passage of red blood cells), while still preventing potential emboli (e.g., atherothrombotic debris) from passing. In various embodiments, the embolism protection device may have an elongated shape, with a total length of about 10-15 cm, and an expanded width of about 3-7 mm.

Figure 1B:
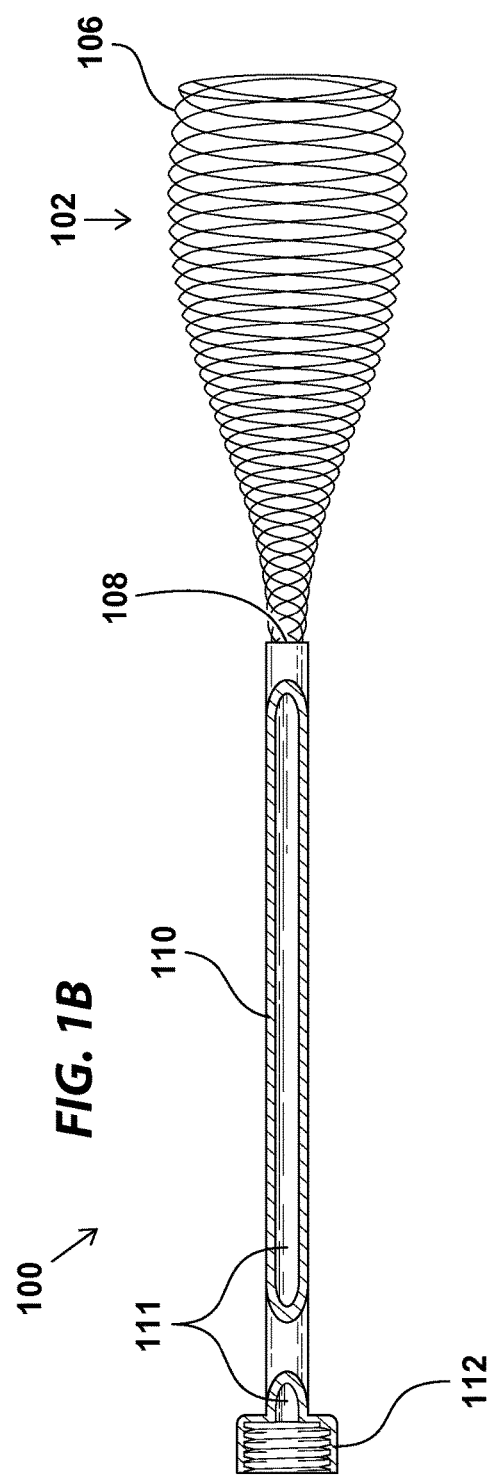

FIGS. 1A and 1B illustrate an example of an embolism protection device in an expanded state, shown in a perspective view (FIG. 1A) and a partial cutaway view (FIG. 1B), in accordance with various embodiments. As shown in FIG. 1A, the embolism protection device 100 may include a first (distal) portion 102 that may be formed from a compliant mesh material 104 and a compliant wire support member 106 that biases the first portion 102 into a funnel having a generally conical or cup-like shape. In various embodiments, the first portion 102 may be sized and shaped such that it may be inserted into an artery of the foot in a compressed state, and it may be biased such that it naturally assumes a cone or cup shape when released. In various embodiments, the outer diameter of the distal portion 102 may be sized and shaped to abut the walls of the artery when in an open state.

In various embodiments, the first portion 102 may be formed from a thin, hydrophilic, compliant mesh material 104 having a pore size that is sufficiently large to allow red blood cells and other blood components to flow freely therethrough, but that is sufficiently small to prevent potential thrombi and emboli from passing through. For example, in some embodiments, the compliant mesh material 104 may have a pore size of from about 80 microns to about 100 microns, or from about 90 microns to about 100 microns. In various embodiments, a compliant wire support member 106 may be disposed within or otherwise coupled to the funnel-shaped compliant mesh material 104, such that it provides support to the compliant mesh material 104 and helps to support and form the compliant mesh material 104 in the generally conical or cup shape. In various embodiments, the compliant wire support member 106 may be formed from a material having a shape memory function, such as Nitinol™ wire, and may be biased to assume an open configuration.

As shown in FIG. 1B, the first portion 102 of the embolism protection device 100 may include an aperture 108 at the apex or base of the funnel that extends to form (or couples to) a slender, solid-walled catheter portion 110 having a lumen 111 extending therethrough. In some embodiments, the aperture 108 in the apex of the cone or cup shaped first portion 102 may communicate with the lumen of the catheter portion 110, for example, so that debris captured in the compliant mesh material 104 may be evacuated from the body via the catheter portion 110. In some embodiments, the proximal end of the catheter portion (e.g., the end nearest the physician and outside the body) may include a threaded or Luer-lock coupling mechanism 112, for example for coupling to a syringe or stopcock. In some embodiments, the syringe or stopcock may be used to draw debris captured by the embolism protection device through the catheter portion and out of the body.

FIGS. 2A and 2B include an exploded view (FIG. 2A) and a cross-sectional view (FIG. 2B) illustrating how the embolism protection device shown in FIGS. 1A and 1B may be maintained in a compressed state inside a deployment catheter, in accordance with various embodiments. In some embodiments, the embolism protection device 100 may be collapsed when it is inserted into a narrow-diameter catheter, such as the illustrated deployment/retrieval catheter 120. As shown in FIG. 2B, in some embodiments, the catheter portion 110 of the compressed embolism protection device 100 may extend beyond the proximal end of the deployment catheter 120, and may be grasped or manipulated by a user, for example during placement of the device.

FIG. 3 illustrates the embolism protection device shown in FIGS. 1A and 1B in the process of being deployed from the deployment catheter, in accordance with various embodiments. One the deployment/retrieval catheter 120 has been advanced to a desired position within the desired artery, such as the dorsalis pedis, the embolism protection device 100 may be unsheathed and allowed to expand. In various embodiments, because the compliant wire support member 106 is biased in an open position, withdrawing the deployment catheter 120 while leaving the embolism protection device 100 in place may allow the compliant wire support member 106 to expand the first portion 102 as it is released from the deployment catheter 120.

Figure 4A:
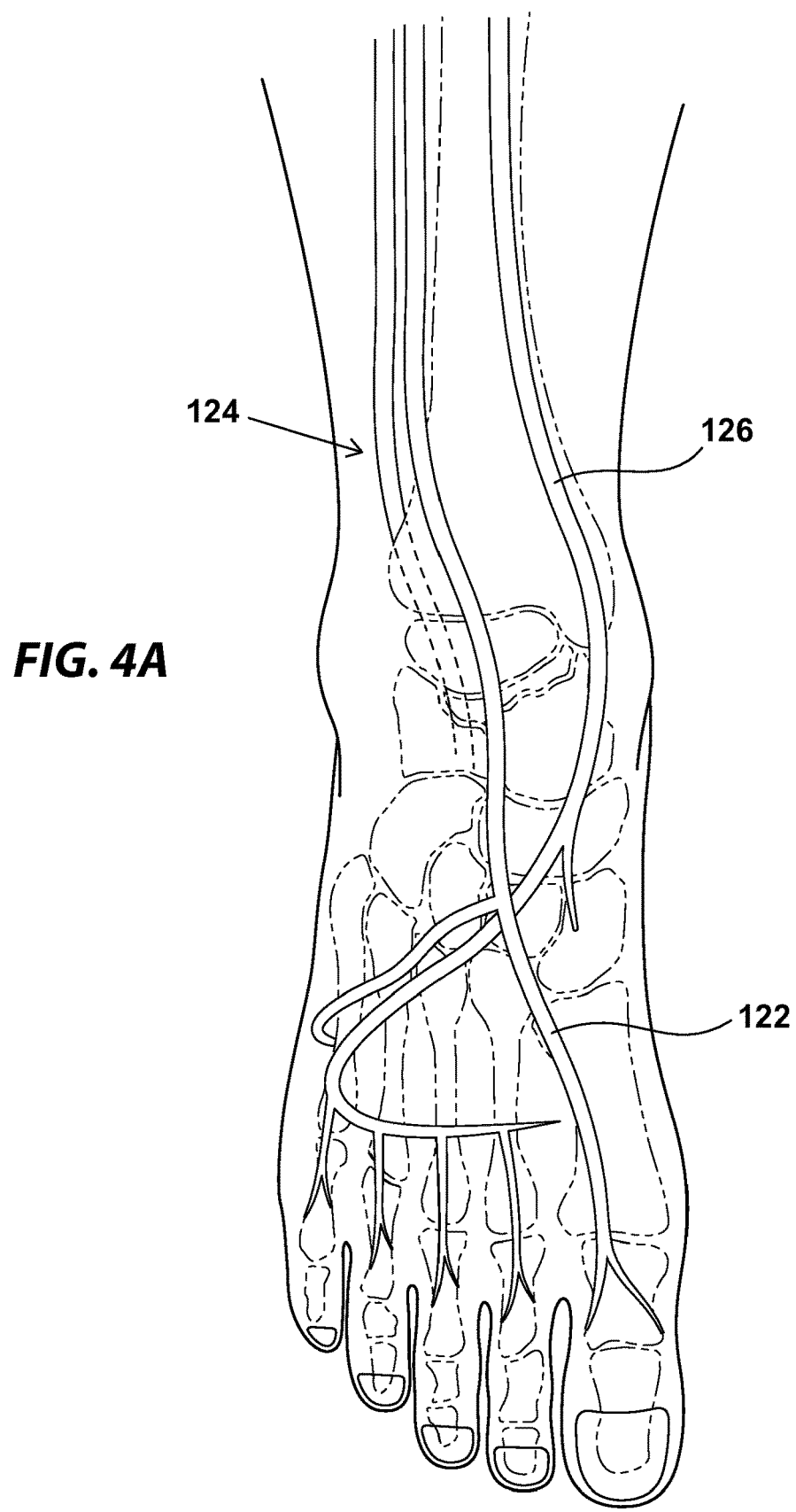
FIGS. 4A and 4B illustrate the major arteries of the foot (FIG. 4A) and an example of a method of using the embolism protection device of FIGS. 1A and 1B in the dorsalis pedis artery during an intervention on a CTO upstream of the device (FIG. 4B)
Figure 4B:
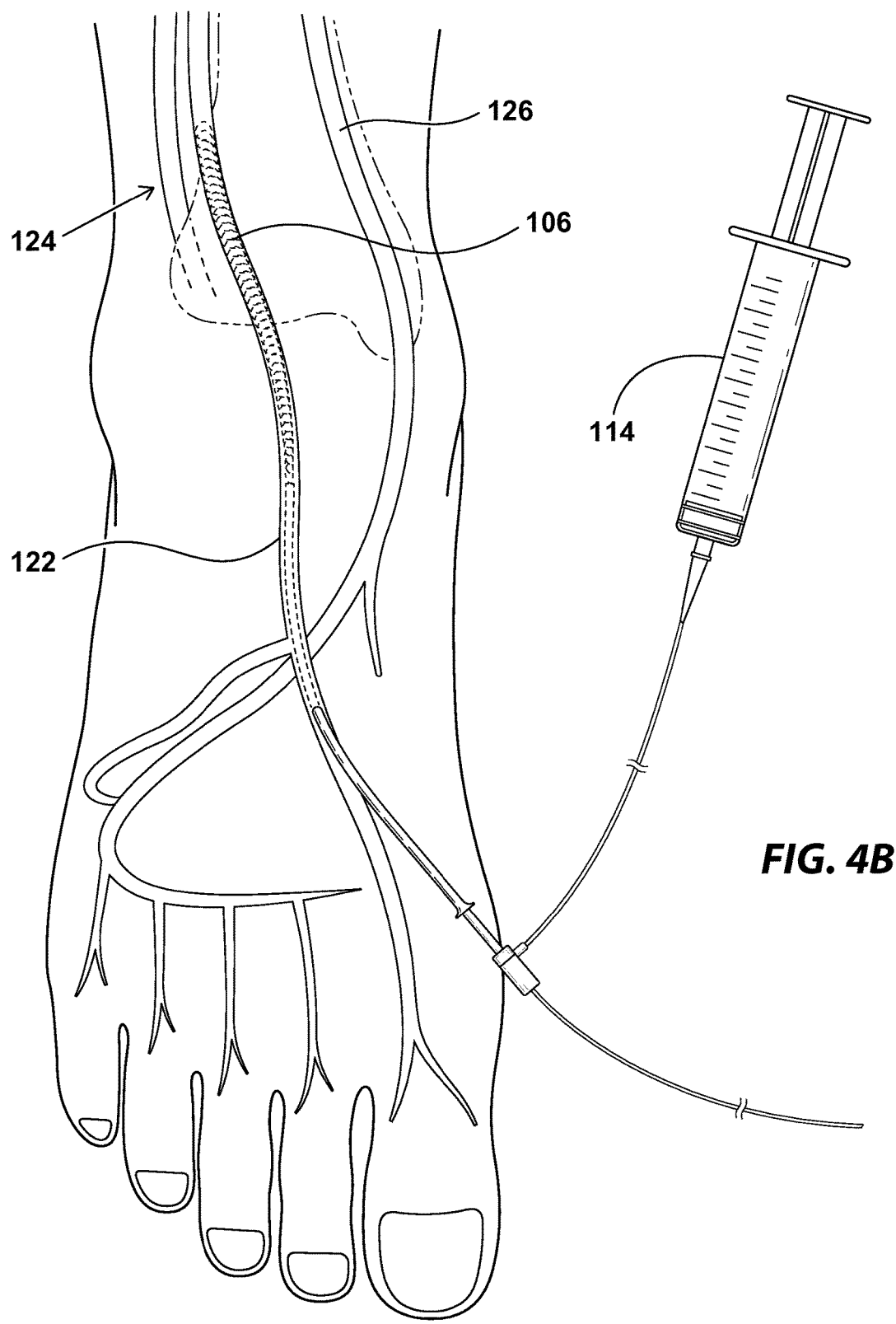

FIGS. 4A and 4B illustrate the major arteries of the foot (FIG. 4A) and an example of a method of using the embolism protection device of FIGS. 1A and 1B in the dorsalis pedis artery during an intervention on a CTO upstream of the device (FIG. 4B), in accordance with various embodiments. Depending on the location of the CTO in the subject, and the particular vascular anatomy of the subject, the embolism protection device 100 may be deployed in the dorsalis pedis 122 as illustrated in FIG. 4B, or it may be deployed in the posterior tibialis 124 or peroneal (fibular) artery 126. In various embodiments, any of these arteries may receive the embolism protection devices disclosed herein, and may be selected based on proximity to the lesion being treated. As illustrated in FIG. 4B, once the embolism protection device 100 has been deployed in a desired artery, the deployment catheter 120 may be withdrawn to allow the compliant wire support member 106 to expand within the artery 122, thus abutting and contacting the full circumference of the arterial wall.

The intervention may then be performed upstream at the site of the occlusion via equipment that is advanced from the femoral artery, and any debris generated from the intervention may be captured by the compliant mesh material of the embolism protection device 100. If desired, in some embodiments, any captured debris may be withdrawn from the body through the embolism protection device, for example via a syringe 114. Once the intervention is complete, the embolism protection device 100 may be withdrawn from the artery 122. In some embodiments, prior to removal, the deployment catheter 102 may be advanced over the compliant wire support member 106, thereby collapsing the embolism protection device 100 prior to removal. In other embodiments, the embolism protection device 100 may be simply pulled from the artery 122 because, due to its compliant nature, it may be removed atraumatically even in the expanded state.

Figure 5:
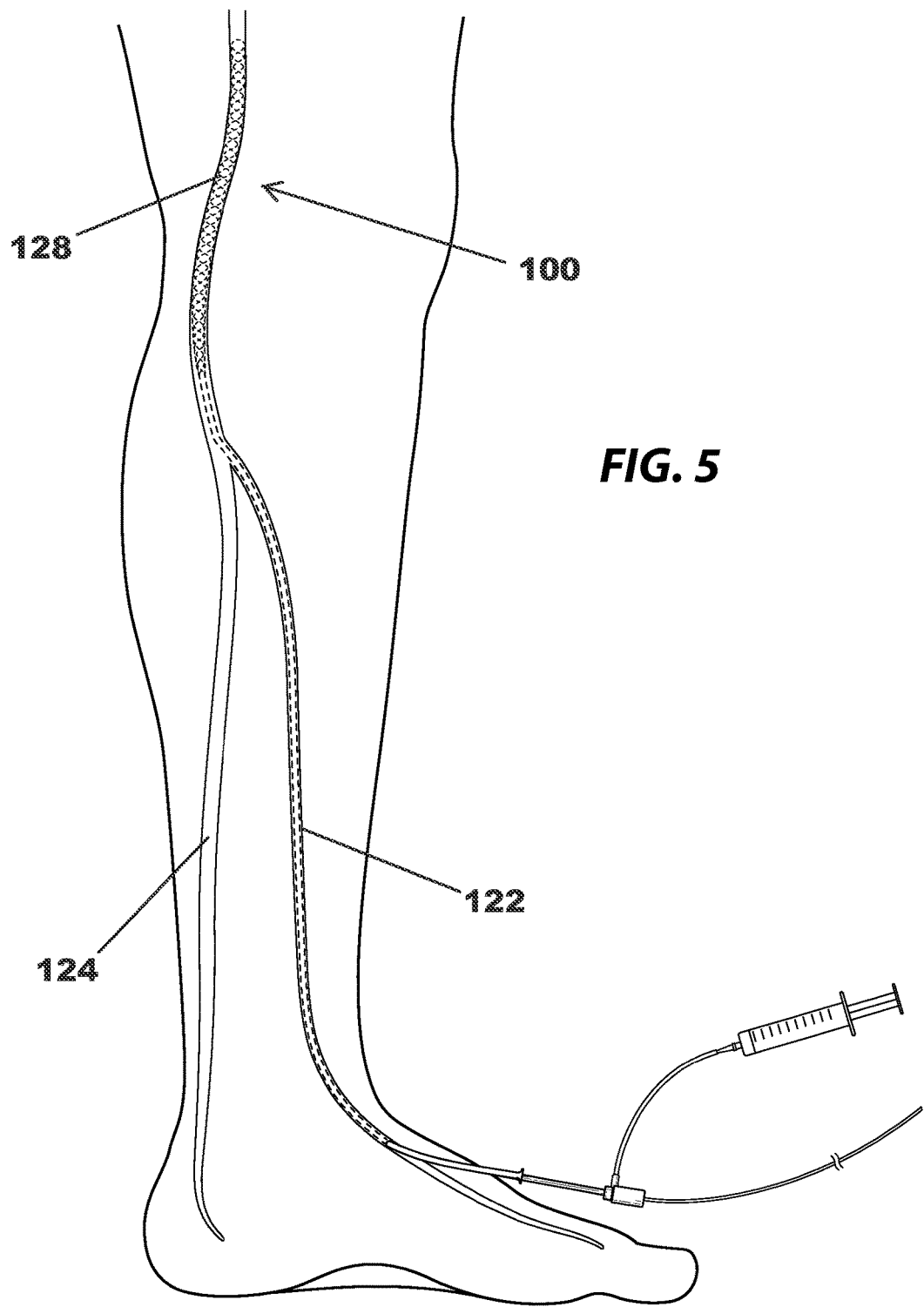
FIG. 5 illustrates an example of using the embolism protection device of FIGS. 1A and 1B in the popliteal artery.

FIG. 5 illustrates another example of using the embolism protection device of FIGS. 1A and 1B, wherein the embolism protection device is placed in the popliteal artery. In some embodiments, it may be advantageous to advance the embolism protection device 100 further proximally (e.g., further up the leg, towards the trunk) in order to protect multiple arteries and arterial branches in the foot and lower leg when the occlusion is located more praximally, such as in the superficial femoral artery. In these embodiments, the embolism protection device 100 may be advanced through one of the arteries of the foot, such as the dorsalis pedis 122, posterior tibialis 124, or peroneal (fibular) artery (not shown) until it reaches the popliteal artery 128. Once it has been positioned in this fashion, the device may be deployed and used as described above with reference to FIGS. 4A and 4B.

Figure 6A:
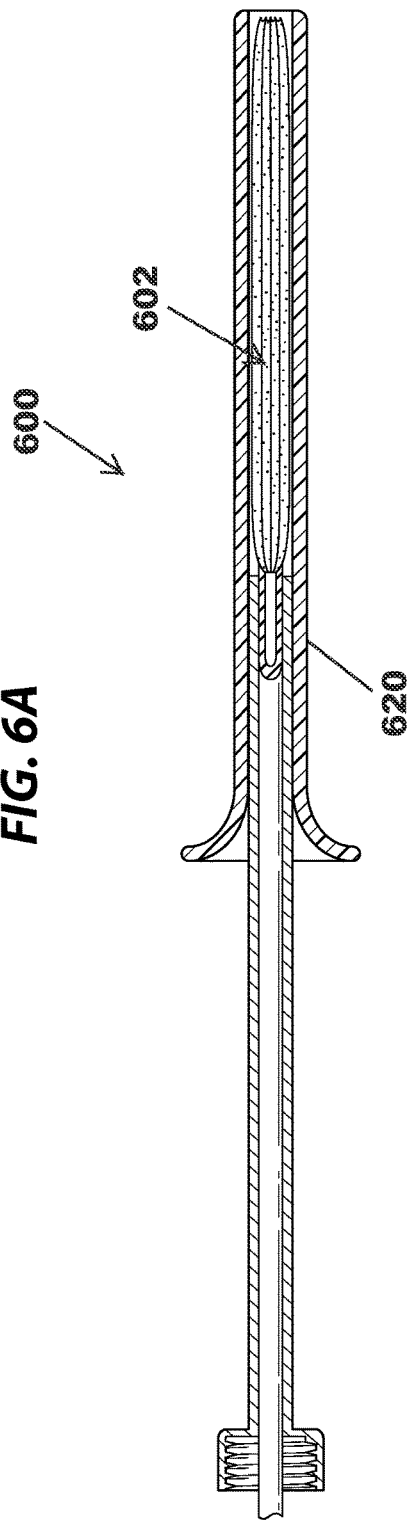
FIGS. 6A and 6B illustrate an example of an embolism protection device having a plurality of longitudinal compliant support members shown in the closed (FIG. 6A) and open (FIG. 6B) positions, all in accordance with various embodiments.
Figure 6B:
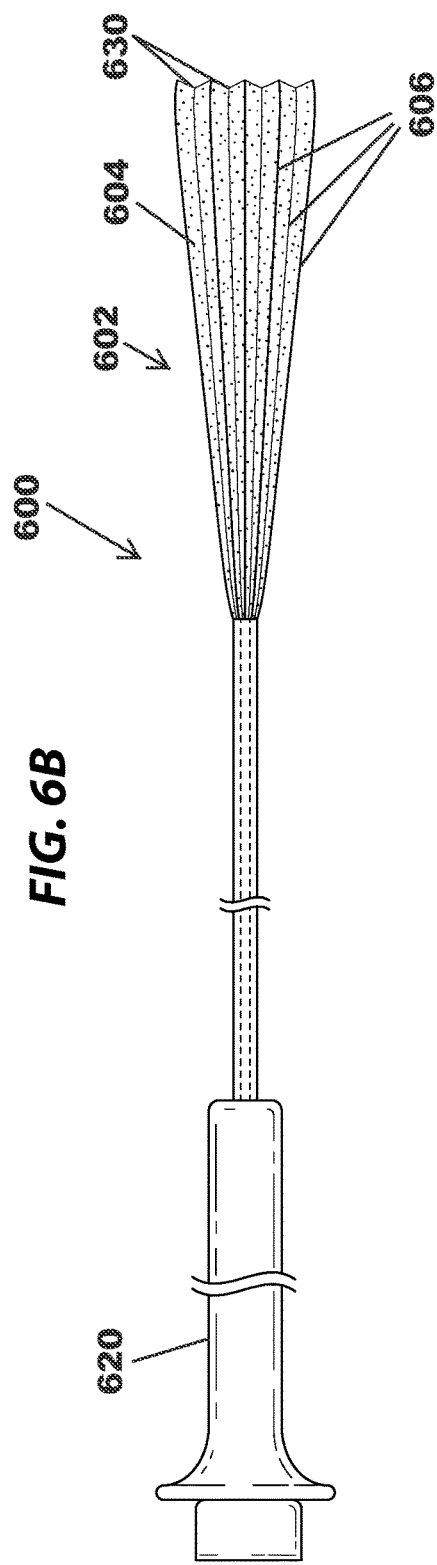

FIGS. 6A and 6B illustrate an example of an embolism protection device having a plurality of longitudinal compliant support members shown in the closed (FIG. 6A) and open (FIG. 6B) positions, in accordance with various embodiments. In various embodiments, instead of the spiral-shaped compliant support members shown in FIGS. 1A and 1B, the embolism protections device 600 may instead include a plurality of longitudinal compliant support members 606 that may be biased in an open position (FIG. 6B), such that they open the first portion 602 of the embolism protection device 600 when released from the deployment catheter 620, stretching the compliant mesh 604 into a funnel or inverted umbrella shape. In some embodiments, the compliant mesh 604 may include a plurality of longitudinal pleats 630 corresponding to each of the plurality of longitudinal compliant support members 606, which pleats 630 allow the first portion 602 to compress tightly and fit within the deployment catheter 620 (FIG. 6A).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of protecting a subject from embolism during a peripheral artery procedure, comprising:
    advancing a guidewire through the vasculature of the subject through a puncture site in an artery of a foot, wherein the puncture site is distal to a peripheral arterial lesion;
    advancing a catheter and an embolism protection device compressed within the catheter along the guidewire to a position adjacent the peripheral arterial lesion, the catheter having a proximal end and a distal end;
    wherein the embolism protection device comprises:
        a compliant mesh portion comprising a funnel shape and having an open distal end and a proximal apex generally opposite the open distal end, the compliant mesh portion having a pore size selected to allow blood to pass therethrough while restricting the passage of potential emboli;
        a compliant wire support member comprising a material having a shape-memory function; the compliant wire support member being coupled to the compliant mesh portion and biasing the compliant mesh portion in an open position;
        a catheter portion coupled to and extending from the apex and having a lumen in communication with an aperture in the apex;
        wherein the embolism protection device has a collapsed state wherein the embolism protection device fits within the lumen of a deployment catheter, and an expanded state wherein the compliant mesh portion is sized to span the width of an artery of the foot;
    withdrawing the catheter through the puncture site in the artery of the foot, thereby allowing the embolism protection device to self-expand;
    performing the peripheral artery procedure; and
    removing the embolism protection device from the vasculature of the subject.

2. The method of claim 1, wherein the artery of the foot is a dorsalis pedis, a posterior tibialis, or a peroneal (fibular) artery.

3. The method of claim 1, wherein the steps of (1) advancing a catheter along the guidewire to a position adjacent a peripheral arterial lesion; and (2) advancing an embolism protection device compressed within the catheter occur simultaneously.

4. The method of claim 1, wherein the steps of (1) advancing a catheter along the guidewire to a position adjacent a peripheral arterial lesion; and (2) advancing an embolism protection device compressed within the catheter occur sequentially.

5. The method of claim 1, wherein the method further comprises coupling an evacuation device to a proximal end of the catheter portion of the embolism protection device.

6. The method of claim 5, wherein the method further comprises using the evacuation device to remove debris from the embolism protection device.

* * * * *